United States Patent
Shelton, IV et al.

(10) Patent No.: US 11,224,460 B2
(45) Date of Patent: *Jan. 18, 2022

(54) ACCESS DEVICE

(71) Applicant: Cilag GmbH International

(72) Inventors: Frederick E. Shelton, IV, Hillsboro, OH (US); Christopher W. Widenhouse, Clarksville, OH (US)

(73) Assignee: Cilag GmbH International, Zug (CH)

( * ) Notice: Subject to any disclaimer, the term of this patent is extended or adjusted under 35 U.S.C. 154(b) by 16 days.

This patent is subject to a terminal disclaimer.

(21) Appl. No.: 16/059,689

(22) Filed: Aug. 9, 2018

(65) Prior Publication Data

US 2018/0344352 A1 Dec. 6, 2018

Related U.S. Application Data

(63) Continuation of application No. 15/469,040, filed on Mar. 24, 2017, now abandoned, which is a continuation of application No. 15/207,133, filed on Jul. 11, 2016, now abandoned, which is a continuation of application No. 14/683,306, filed on Apr. 10, 2015, now abandoned, which is a continuation of application No. 12/712,276, filed on Feb. 25, 2010, now Pat. No. 9,005,116, which is a continuation-in-part of application No. 12/479,418, filed on Jun. 5, 2009, now Pat. No. 8,357,085.

(60) Provisional application No. 61/165,080, filed on Mar. 31, 2009.

(51) Int. Cl.
*A61B 17/34* (2006.01)
*A61B 17/02* (2006.01)

(52) U.S. Cl.
CPC ...... *A61B 17/3423* (2013.01); *A61B 17/0218* (2013.01); *A61B 17/0293* (2013.01); *A61B 17/3431* (2013.01); *A61B 2017/0225* (2013.01); *A61B 2017/3429* (2013.01); *A61B 2017/3445* (2013.01); *A61B 2017/3447* (2013.01); *A61B 2017/3466* (2013.01)

(58) Field of Classification Search
CPC ........ A61B 17/3423; A61B 2017/3435; A61B 2017/3427; A61B 2017/3429; A61B 2017/3445; A61B 2017/345; A61B 2017/3466
See application file for complete search history.

(56) References Cited

U.S. PATENT DOCUMENTS

| | | | |
|---|---|---|---|
| 5,545,179 A * | 8/1996 | Williamson, IV | A61B 17/3423 600/32 |
| 6,551,270 B1 * | 4/2003 | Bimbo | A61B 17/3421 604/167.03 |
| 2006/0247678 A1* | 11/2006 | Weisenburgh, II | A61B 17/0281 606/205 |

* cited by examiner

*Primary Examiner* — Anu Ramana

(57) ABSTRACT

Various devices and methods are provided with respect to inserting multiple surgical instruments through a single surgical access device. A medical device including a flexible tissue retractor a releasable insert having multiple instrument openings, and a member such as a sleeve is disclosed. The insert can be in the form of an insert assembly including multiple components. The sleeve can support the insert with respect to the retractor such that the insert and sleeve can be removed together with the retractor remaining in the incision. A method of using the insert is also described.

15 Claims, 13 Drawing Sheets

ACCESS DEVICE

CROSS REFERENCE TO RELATED APPLICATIONS

This application is a continuation of U.S. patent application Ser. No. 15/469,040, filed on Mar. 24, 2017, which is a continuation of Ser. No. 15/207,133, filed on Jul. 11, 2016, now abandoned, which is a continuation of U.S. patent application Ser. No. 14/683,306, filed Apr. 10, 2015, now abandoned, which is a continuation of U.S. patent application Ser. No. 12/712,276, filed Feb. 25, 2010, now U.S. Pat. No. 9,005,116, which is a continuation-in-part of U.S. patent application Ser. No. 12/479,418, filed Jun. 5, 2009, now U.S. Pat. No. 8,357,085, which claims the benefit of U.S. Provisional Patent Application Ser. No. 61/165,080, filed on Mar. 31, 2009.

The present application cross references and incorporates by reference the following commonly assigned US patent applications: U.S. Ser. No. 11/398,985 filed Apr. 5, 2006 and issued as U.S. Pat. No. 8,545,450; U.S. Ser. No. 11/399,181 filed Apr. 5, 2006 and issued as U.S. Pat. No. 7,837,612; U.S. Ser. No. 11/399,145 filed Apr. 5, 2006 and published as US2006/0247678; U.S. Ser. No. 11/399,149 filed Apr. 5, 2006 and published as US2006/0270911; U.S. Ser. No. 11/399,044 filed Apr. 5, 2006 and published as US2006/0247586; U.S. Ser. No. 11/399,172 filed Apr. 5, 2006 and published as US2006/0247500; U.S. Ser. No. 11/399,045 filed Apr. 5, 2006 and published as US20060/247516; U.S. Ser. No. 12/242,765 filed Sep. 30, 2008 and published as US2010/0081880; U.S. Ser. No. 12/242,711 filed Sep. 30, 2008 and issued as U.S. Pat. No. 8,485,970; U.S. Ser. No. 12/242,721 filed Sep. 30, 2008 and issued as U.S. Pat. No. 8,430,811; U.S. Ser. No. 12/242,383 filed Sep. 30, 3008 and issued as U.S. Pat. No. 8,206,294; U.S. Ser. No. 12/242,333 filed Sep. 30, 2008 and published as US20100081863; U.S. Ser. No. 12/242,353 filed Sep. 30, 2008 and published as US20100081864; U.S. Ser. No. 12/242,381 filed Sep. 30, 2008 and published as US20100081883; U.S. Ser. No. 12/399,625 filed Mar. 6, 2009 and published as US20100228091; U.S. Ser. No. 12/399,633 filed Mar. 6, 2009 and issued as U.S. Pat. No. 8,821,391; U.S. Ser. No. 12/399,547 filed Mar. 6, 2009 and issued as U.S. Pat. No. 8,251,900; U.S. Ser. No. 12/399,656 filed Mar. 6, 2009 published as US2010/0228094; U.S. Ser. No. 12/399,482 filed Mar. 6, 2009 and published as US2010/0228096; U.S. Ser. No. 12/399,473 and published as US2010/0228090; U.S. Ser. No. 12/110,724 filed Apr. 28, 2008 and issued as U.S. Pat. No. 8,579,807; U.S. Ser. No. 12/109,881 filed Apr. 25, 2008 and issued as U.S. Pat. No. 8,690,831; and U.S. Ser. No. 12/172,349 filed Jul. 14, 2008 and published as US20100010310.

FIELD OF INVENTION

The present invention relates to access devices, such as for providing surgical access into a body cavity.

BACKGROUND

Abdominal laparoscopic surgery gained popularity in the late 1980[1]s, when benefits of laparoscopic removal of the gallbladder over traditional (open) operation became evident Reduced postoperative recovery time, markedly decreased post-operative pain and wound infection, and improved cosmetic outcome are well established benefits laparoscopic surgery, derived mainly from the ability of laparoscopic surgeons to perform an operation utilizing smaller incisions of the body cavity wall.

Laparoscopic procedures generally involve insufflation of the abdominal cavity with $CO_2$ gas to a pressure of around 15 mm Hg. The abdominal wall is pierced and a 5-10 mm in diameter straight tubular cannula or trocar sleeve is then inserted into the abdominal cavity. A laparoscopic telescope connected to an operating room monitor is used to visualize the operative field, and is placed through a trocar sleeve. Laparoscopic instruments (graspers, dissectors, scissors, retractors, etc.) are placed through two or more additional trocar sleeves for the manipulations by the surgeon and surgical assistant(s).

Recently, so-called "mini-laparoscopy" has been introduced utilizing 2-3 mm diameter straight trocar sleeves and laparoscopic instruments. When successful, mini-laparoscopy allows further reduction of abdominal wall trauma and improved consmesis. Instruments used for mini-laparoscopic procedures are, however, generally more expensive and fragile. Because of their performance limitations, due to their smaller diameter (weak suction-irrigation system, poor durability, decreased video quality), mini-laparoscopic instruments can generally be used only on selected patients with favorable anatomy (thin cavity wall, few adhesions, minimal inflammation, etc.). These patients represent a small percentage of patients requiring laparoscopic procedures. In addition, smaller 2-3 mm incisions may still cause undesirable cosmetic outcomes and wound complications (bleeding, infection, pain, keloid formation, etc.).

Since the benefits of smaller and fewer body cavity incisions are proven, it would be desirable to perform an operation utilizing only a single incision in the navel. An umbilicus is well-hidden and the thinnest and least vascularized area of the abdominal wall. The umbilicus is generally a preferred choice of abdominal cavity entry m laparoscopic procedures. An umbilical incision can be easily enlarged (in order to eviscerate a larger specimen) without significantly compromising cosmesis and without increasing the chances of wound complications. The placement of two or more standard (straight) cannulas and laparoscopic instruments in the umbilicus, next to each other, creates a so-called "chopstick" effect, which describes interference between the surgeon's hands, between the surgeon's hands and the instruments, and between the instruments. This interference greatly reduces the surgeon's ability to perform a described procedure.

Thus, there is a need for instruments and trocar systems which allow laparoscopic procedures to be performed entirely through the umbilicus or a surgical port located elsewhere while at the same time reducing or eliminating the "chopstick effect."

SUMMARY OF THE INVENTION

The present invention generally provides devices for allowing surgical access to an interior of a patient's body.

In one embodiment, the medical device comprises a tissue retractor and an insert releasably supported within a passageway associated with the tissue retractor. The insert may have an outer surface sized and shaped to deform a flexible member of the tissue retractor to provide at least a portion of the passageway with a predetermined size and shape.

The insert can be in the form of an insert assembly having a generally cylindrical outer surface sized to radially stretch a portion of the tissue retractor to have a generally circular or other suitable cross-section of predetermined diameter or width upon insertion of the insert within the passageway.

The tissue retractor may be a flexible tissue retractor which includes a flexible member, such as a flexible membrane, having a first end and a second end, and the insert may be releasably supported or otherwise releasably insertable within the passageway of the flexible tissue retractor.

In one embodiment, the insert comprises an assembly having an inner portion and an outer portion. The outer portion can have a generally cylindrical outer surface adapted to engage the inner surface of the passageway of the tissue retractor, and the inner portion may include a plurality of instrument openings aligned with instrument passageways rotatable with respect to the outer portion of the insert and the flexible tissue retractor.

The insert may comprise an assembly which includes an outer body portion sized and shaped to engage and deform a portion of the inner surface of a flexible tissue retractor, a housing disposed at least partially within the outer sleeve, at least one instrument opening in an upper surface of the housing, and at least one seal operatively associated with each instrument opening. The insert assembly may also include an instrument channel member in the form of a unitary, flexible structure defining a plurality of tubular instrument channels. Each tubular instrument channel may be independently deformable with respect to the housing and the other tubular instrument channels. The instrument channels and instrument openings may be rotatably supported with respect to the outer sleeve and the tissue retractor, such as by a bearing member.

In one embodiment, the flexible tissue retractor comprises first and second deformable rings, and the insert is sized and shaped to pass through at least one of the rings without deforming the ring. The insert may be sized and shaped to deform a portion of a flexible member extending intermediate the first and second rings.

In on embodiment, an assembly comprising a flexible tissue retractor, an insert, and a sleeve is provided. The sleeve may be positioned in the flexible tissue retractor, and the insert may be pressed into the sleeve. The sleeve and insert may be removed together from the retractor without removing the retractor from the incision. The sleeve may be provided to assist in inserting and removing the insert, and the sleeve may be formed of a material having a relatively low coefficient of friction, and a relatively high puncture resistance and/or high toughness.

In one embodiment, a method for accessing a body cavity through in incision is provided. The method includes the steps of positioning a tissue retractor in the incision; and releasably positioning an insert having multiple instrument openings into the tissue retractor. The step of positioning the insert may be by pressing the insert into the tissue retractor, and may include deforming and/or stretching at least a portion of the tissue retractor. The method may include forming an incision, positioning a tissue retractor in the incision, positioning a sleeve to extend at least partially within the tissue retractor, and positioning an insert having one or more instrument openings into the sleeve.

In one embodiment, a medical device is provided including a tissue retractor, at least one insert having at least one instrument opening, where the insert is positionable, such as by pressing, at different insertion depths within a passageway of the tissue retractor.

In one embodiment, a method for accessing a body cavity includes the steps of positioning a flexible tissue retractor in the incision, wherein the tissue retractor provides a passageway extending through the incision; releasably positioning a first insert having at least one instrument opening in the passageway provided by the flexible tissue retractor; removing the first insert from the passageway provided by the tissue retractor; and positioning a second insert having at least one instrument opening in the passageway. The second insert can have a different number of instrument openings and/or a different size and/or a different shape than that of the first insert. The method can also include repositioning an insert to a second depth in the passageway of the retractor.

BRIEF DESCRIPTION OF THE DRAWINGS

The invention will be more fully understood from the following detailed description taken in conjunction with the accompanying drawings, in which.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention generally provides a medical device, such as a surgical access assembly, that allows one or more surgical instruments to be inserted through a single incision surgical access device, such as at various depths of insertion, thereby allowing for ease of manipulation of instruments within a patient's body while maintaining insufflation.

Figure 1:
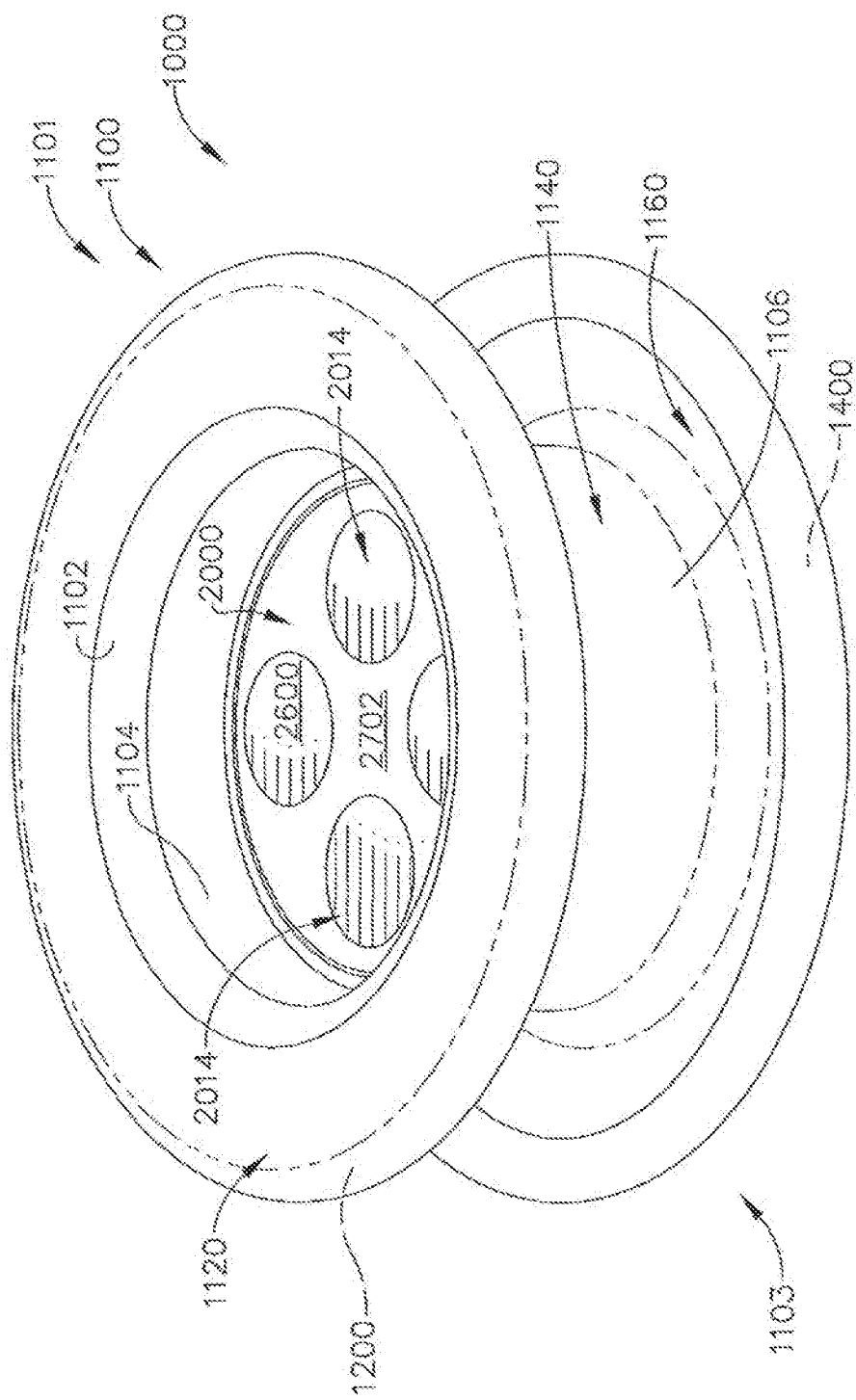
FIG. 1 is a perspective, proximal view showing an access device comprising an insert having at least one instrument opening releasably supported within a flexible tissue retractor, with the proximal end of the insert shown inserted to be positioned below an upper, proximal end of the flexible tissue retractor.
Figure 2:
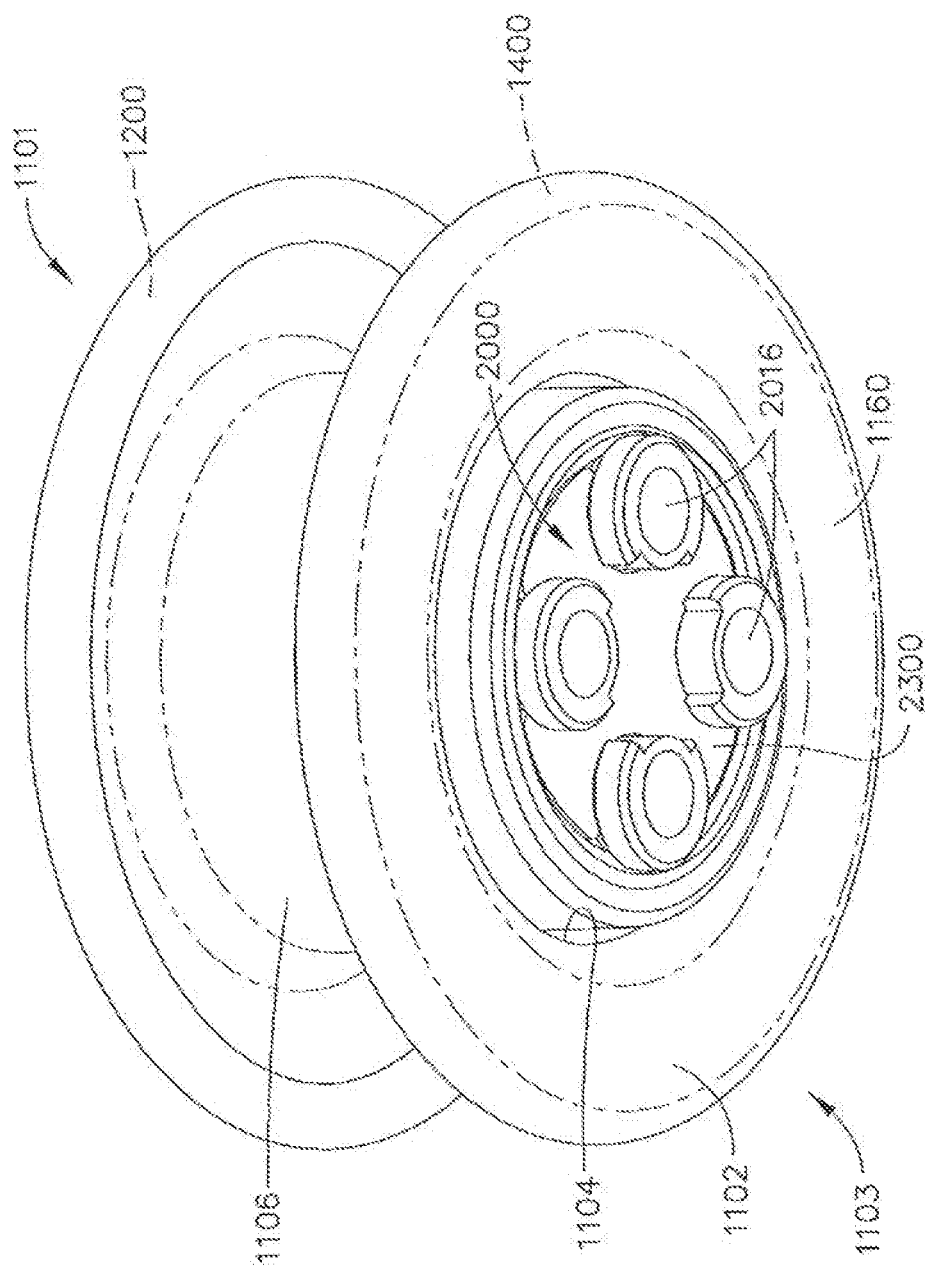
FIG. 2 is a perspective, distal view of the insert and flexible tissue retractor shown in FIG. 1, with a distal, bottom end of the insert shown visible from a lower, distal opening of the flexible tissue retractor.

FIG. 1 is a perspective view of the top, or proximal portion of the access assembly, and FIG. 2 is a perspective view of the bottom, or distal portion of the access assembly. Referring to FIGS. 1 and 2, in one embodiment the medical device is in the form of an access assembly comprising a flexible tissue retractor 1000 and an insert 2000 having at least one instrument opening 2014 (four instrument openings 2014 shown in FIG. 1, and four instrument exits 2016 shown FIG. 2). The instrument openings 2014 may extend through a top surface 2702 of a portion of the insert, and the openings 2014 may be closed or otherwise obstructed by a membrane seal 2600, as described in more detail below.

The insert 2000 is shown releasably supported within a passageway 1104 defined by a flexible member 1100 of the retractor 1000. The phrase "releasably supported" in this context means the insert can be inserted and removed from the tissue retractor multiple times, including during a surgical procedure, without damaging or otherwise impairing the function of the retractor or the insert. In one illustrative example, the insert 2000 is releasably inserted by pressing (such as with a thumb or finger) the insert into the passageway of the retractor.

The flexible member 1100 can include a first generally annular shaped, outer or top portion 1120 (oriented generally horizontally in FIG. 1), a second generally annular shaped, inner portion 1160 (oriented generally horizontally and generally parallel to portion 1120 in FIG. 1), and a generally cylindrically shaped portion 1140 extending axially in a distal direction from portion 1120 to portion 1160.

The outer portion 1120 can be associated with a first, proximal end 1101 of the flexible member 1100, and the inner portion 1160 can be associated with a second, distal end 1103 of the flexible member 110. The outer portion 1120 is disposed outside the patient's body when the flexible retractor is positioned during surgery, and the inner portion 1160 is disposed within the patient, such as within a body cavity, during a surgical procedure. An inner surface of the generally cylindrical portion 1140 may provide most or substantially all of the passageway 1104, while an outer surface of the generally cylindrical portion 1140 may contact the walls of an incision when the flexible retractor 1000 is positioned during surgery, such as is shown in FIG. 3.

The flexible member 1100 may comprise a unitary, flexible membrane forming the portions 1120, 1140, and 1160, and having a first surface 1102 and a second surface 1106. The passageway 1104 of tissue retractor 1000 may be defined at least in part by a portion of the first surface 1102 facing radially inwardly in generally cylindrical portion 1140. The portion of the second surface 1106 associated with the generally cylindrical portion 1140 may face radially outwardly so as to contact or otherwise engage the tissue at the incision site.

The flexible tissue retractor 1000 may also comprise proximal and distal members for providing engagement of outer and inner portions of the retractor with outer and inner portions of the patient. For instance, the tissue retractor 1000 may include a resilient, outer (proximal) deformable ring 1200 and a resilient, inner (distal) deformable ring 1400. Rings 1200 and 1400 are shown in phantom in FIGS. 1 and 2, and in cross-section in FIG. 3. The flexible member 1100 is shown extending intermediate the rings 1200 and 1400, such that member 1100 extends from ring 1200 to ring 1400.

Figure 3:
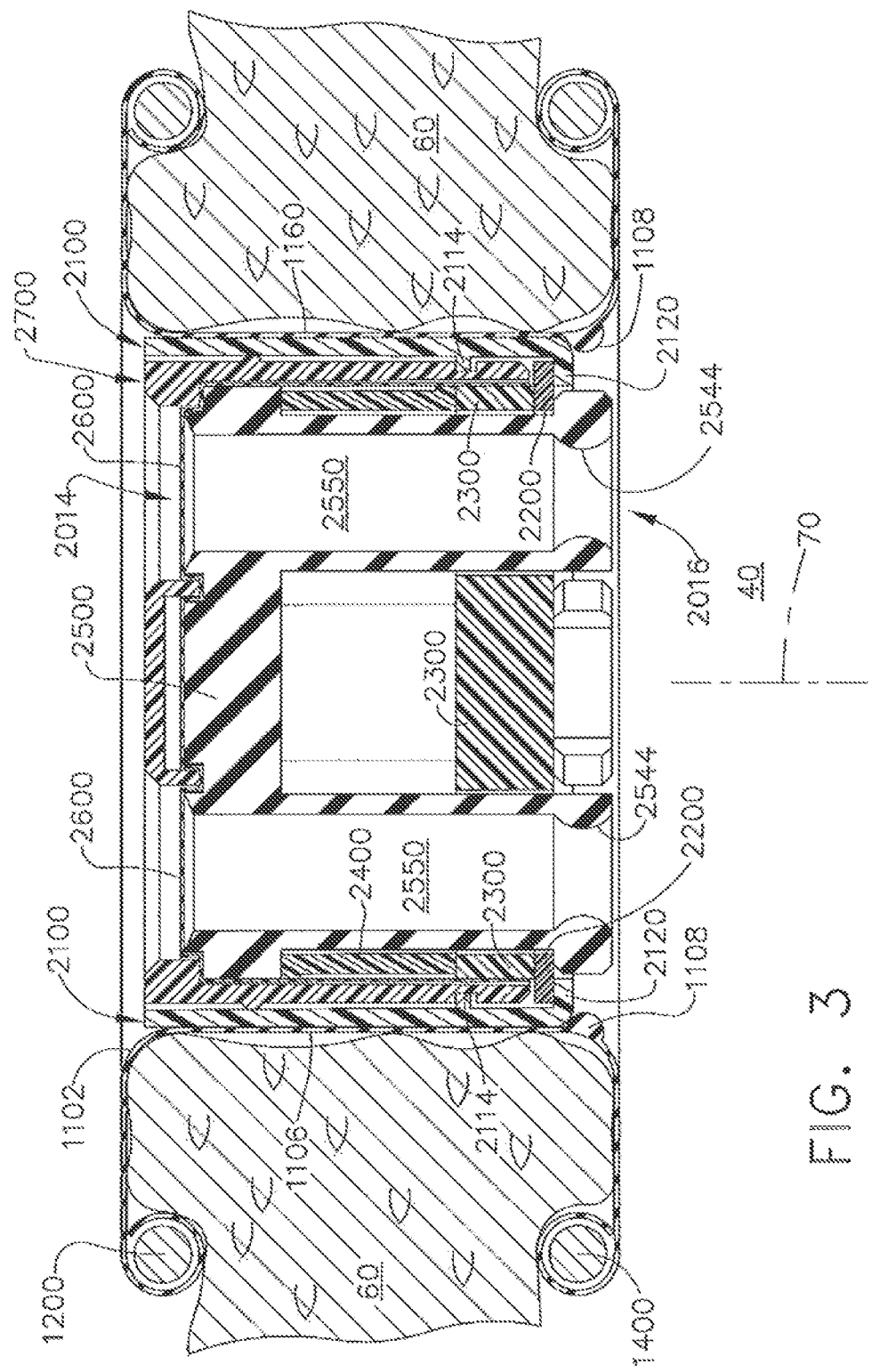
FIG. 3 is a cross-sectional view of a device of the type shown in FIG. 1.

FIG. 3 shows the access assembly of flexible retractor 1000 and insert 2000 positioned in an incision such that the distal portion 1160 of the retractor 1000 and the ring 1400 are disposed in the abdominal cavity 40, and the such that tissue 60 (including a portion of the abdominal wall) engages the surface 1106 of the flexible retractor.

The rings 1200 and 1400 can have any suitable closed or substantially closed configuration, including without limitation circular, oval, and elliptical configurations. By "resilient deformable ring" it is meant that the ring may be relatively easily deformed, such as by pressing opposite sides of the ring together with the fingers (and without any additional tools or aids), so that the ring may be inserted through a narrow incision in a body wall (e.g. the abdominal wall). For instance, the inner ring 1400 may be deformed, such as by pressing opposite sides of the ring together with the fingers, and inserted through an incision in the patient, such as an incision through the abdominal wall. Once the ring is fully inserted, the inner ring 1400 is able to resiliently return to its undeformed shape. The ring assists in securing the retractor 1000 within the incision by engaging the inside surface of the abdominal wall of the abdominal cavity.

The flexible member can comprise a flexible membrane of a resiliently deformable material, such as natural rubber, silicone, or a suitable deformable elastomer or elastomeric material. The deformable rings can be attached to the flexible membrane, or enclosed within rolled ends of the membrane. One suitable flexible tissue retractor comprising a flexible member with inner and outer deformable rings is a tissue retractor available from Hakko as Hakko FF0707.

The flexible tissue retractor can be provided in one or more sizes, and in one example has a length, or height (measured in the direction of axis 70 in FIG. 3) of between about 15 mm and about 30 mm, a maximum diameter corresponding to the diameter of the rings 1200/1400 of about 40 mm to about 80 mm, and an inner passageway diameter of between about 20 mm to about 40 mm. In the figures, the rings are shown having generally the same diameter, but it will be understood that the diameter of the ring 1200 may selected to be greater than that of ring 1400, or the diameter of ring 1200 may be less than that of ring 1400. In one embodiment, a flexible tissue retractor having an inner passageway diameter smaller than that required to permit passage of a user's hand and generally less than about 50 mm can be desirable, so as to provide a access for multiple instruments but without requiring a relatively large incision.

The flexible tissue retractor 1000 may be formed to have a self-supporting predefined shape, such as the shape shown in FIG. 1. By "self-supporting" it is meant that when the retractor 1000 is placed on a substantially horizontal surface (e.g. flat table top), the retractor is able to maintain its shape without collapsing, with the passageway 1104 extending substantially vertically and with the portions 1120 and 1140 separated a predetermined distance from each other by portion 1160.

In FIGS. 1-3, the insert 2000 is shown pressed into or otherwise positioned within a passageway 1104 such that insert 2000 and the instrument openings 2014 are disposed below the ring 1200 and the annular portion 1120 of the flexible tissue retractor. As shown in FIG. 3, a member such as a retention feature in the front of an internal rib 1108 may be formed with or otherwise provide on the internal surface of the retractor. The rib 1108 can be positioned to prevent the insert 2000 from being pushed through the retractor 1000 and into the body cavity 40.

In FIGS. 2 and 3, the distal end of the insert 2000 and the instrument exits 2016 are shown extending generally at or below the distal ring 1400 and the distal portion 1160 of the flexible retractor. Accordingly, the insert 2000 is positioned within the retractor 1000 to provide a low profile, such that the instruments inserted into the openings 2014 and out of the exits 2016 can be pivoted with respect to the insert 2000 and/or each other at pivot points positioned distally of the upper, proximal ring 1200, such as at pivot points positioned within the incision. Such a low profile configuration allows seals associated with the instrument passageways in the insert 2000 to reside below ring 1200, and in particular, within the incision or within the abdominal cavity. Without being limited by theory, it is believed that positioning seals in the abdominal space may assist in preventing the seals from being collapsed or otherwise affected by tissue pressure, and may prevent tissue from closing instrument passageways or otherwise blocking or reducing visibility through the instrument passageways.

Figure 4:
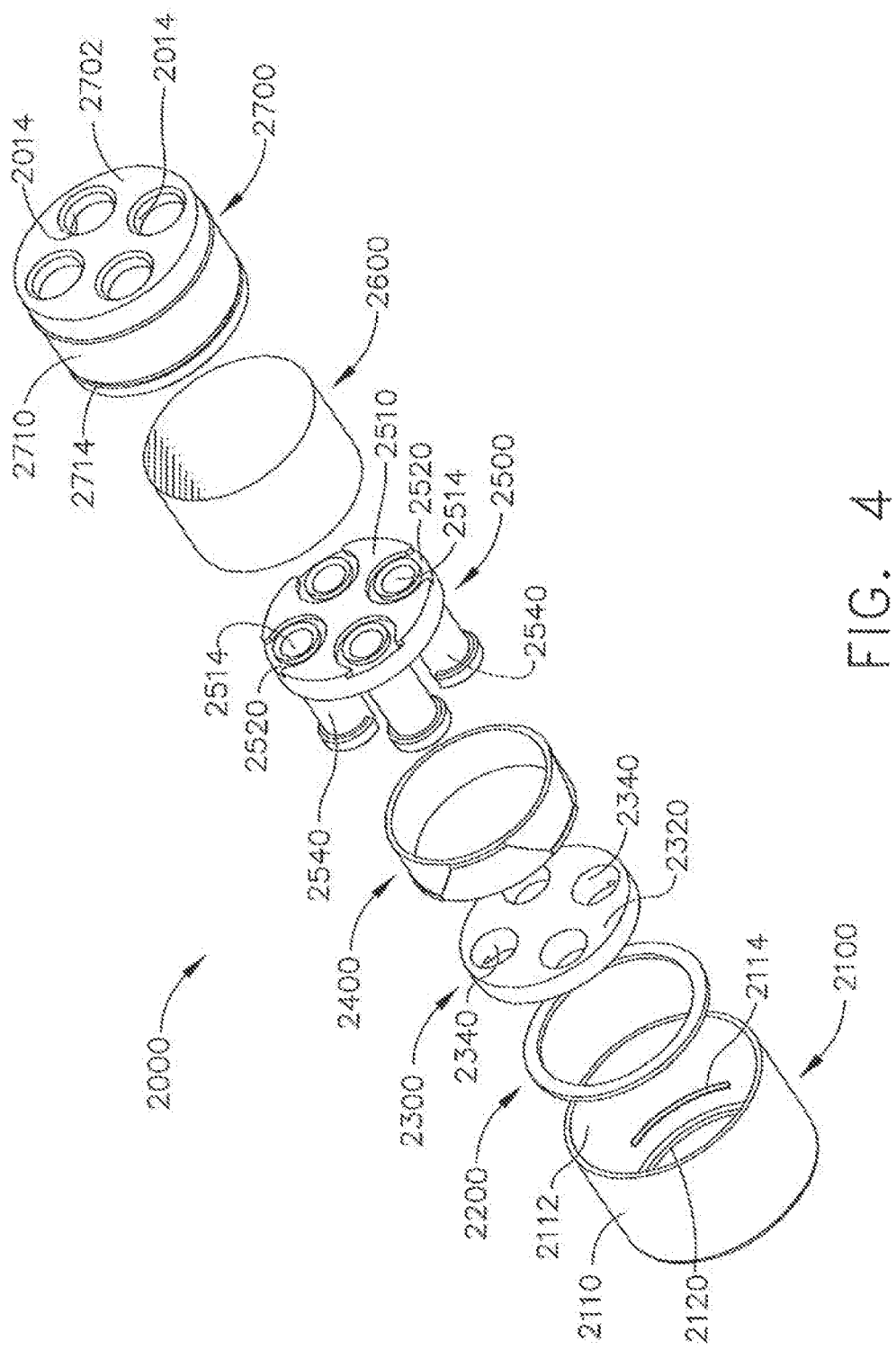
FIG. 4 is an exploded view of an insert of the type shown in FIG. 1.
Figure 5:
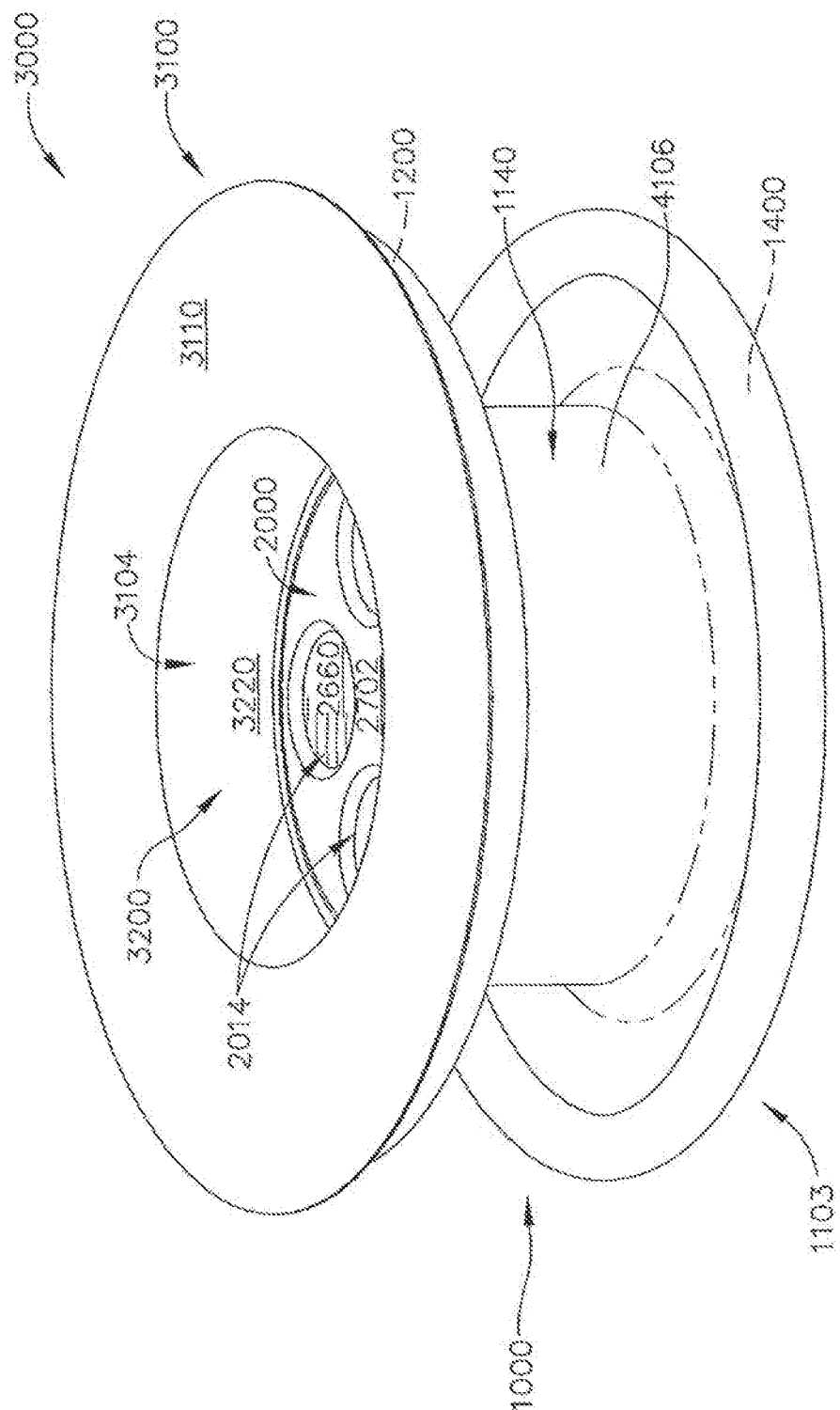
FIG. 5 is a perspective, proximal view showing an alternative access device comprising an assembly of an insert, a flexible tissue retractor, and a sleeve, the sleeve shown as including a generally annular portion disposed over the proximal end of the flexible tissue retractor, and the sleeve shown as including a generally cylindrical portion extending distally from the annular portion, at least a portion of the generally cylindrical portion of the sleeve disposed between the insert and the flexible tissue retractor.
Figure 6:
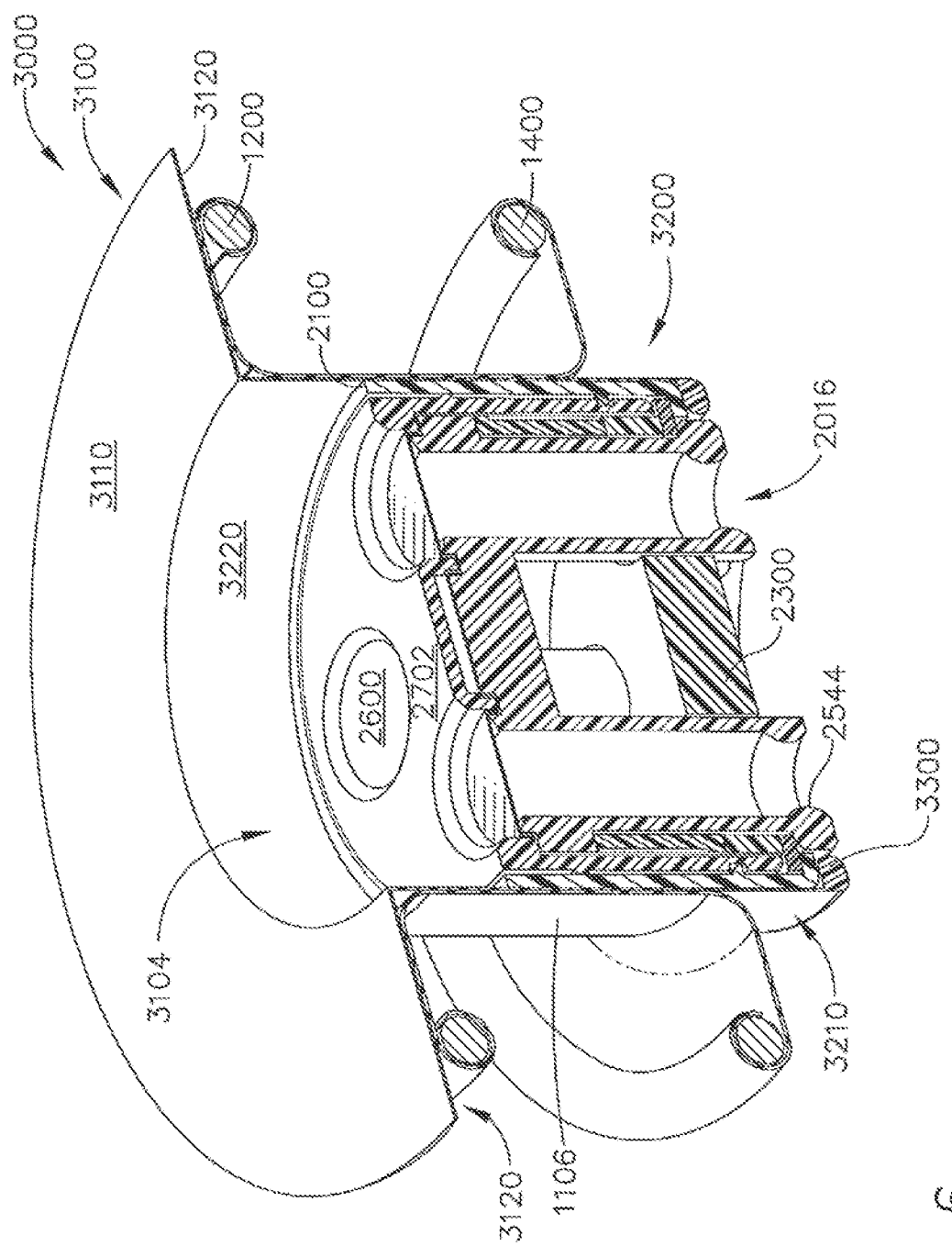
FIG. 6 is a cross-sectional view of the device of the type shown in FIG. 5, and showing the generally cylindrical portion extending distally beyond the distal end of the tissue retractor and the insert, the distal end of the cylindrical portion shown having a member in the form of a generally circumferentially extending rib or ledge for preventing the insert from being pressed into the body cavity and to assist in withdrawing the insert from the tissue retractor.
Figure 7:
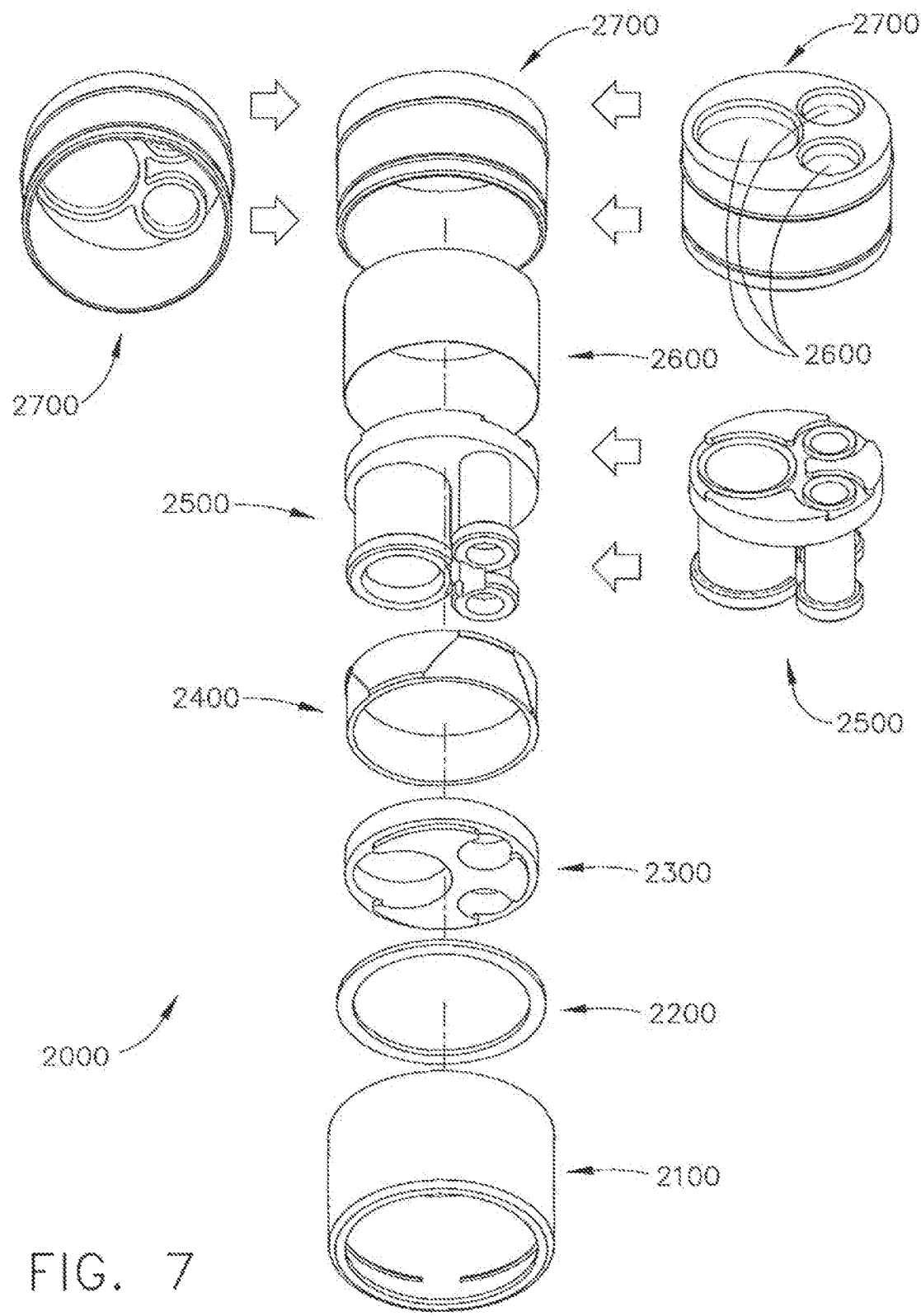
FIG. 7 is a schematic exploded view of an insert similar to that shown in FIG. 4, but having three versus four instrument openings, including one relatively larger instrument opening (such as to receive a laparascope or other relatively larger diameter device), and two relatively smaller instrument openings (such as to receive relatively smaller devices, such as 5 mm graspers, clip appliers, or the like).
Figure 8:
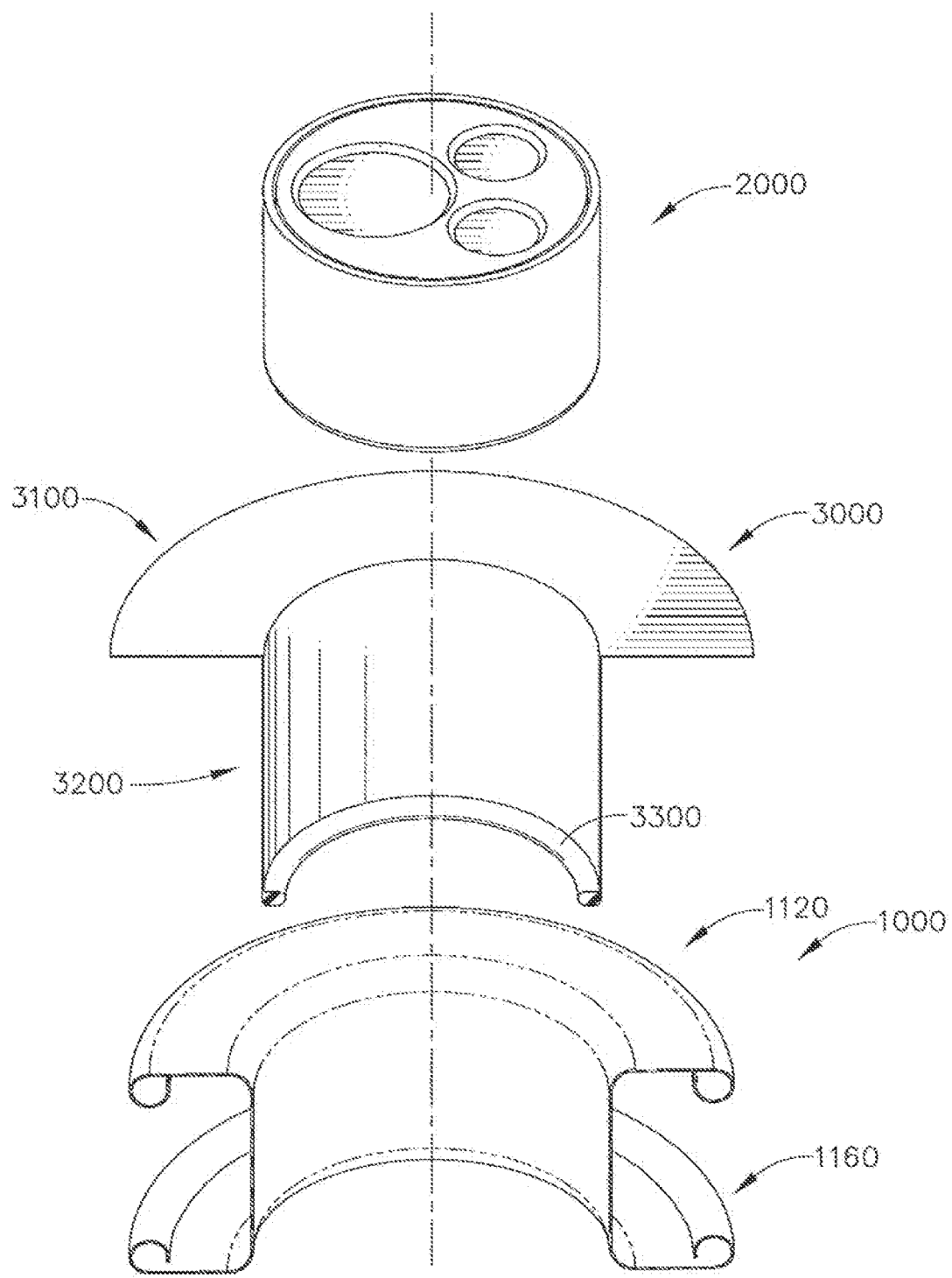
FIG. 8 is a schematic depiction of how the insert of FIG. 7 can be inserted into a sleeve (shown in half section), and the insert and sleeve can, in turn, be inserted into a flexible tissue retractor (also shown in half section).
Figure 9:
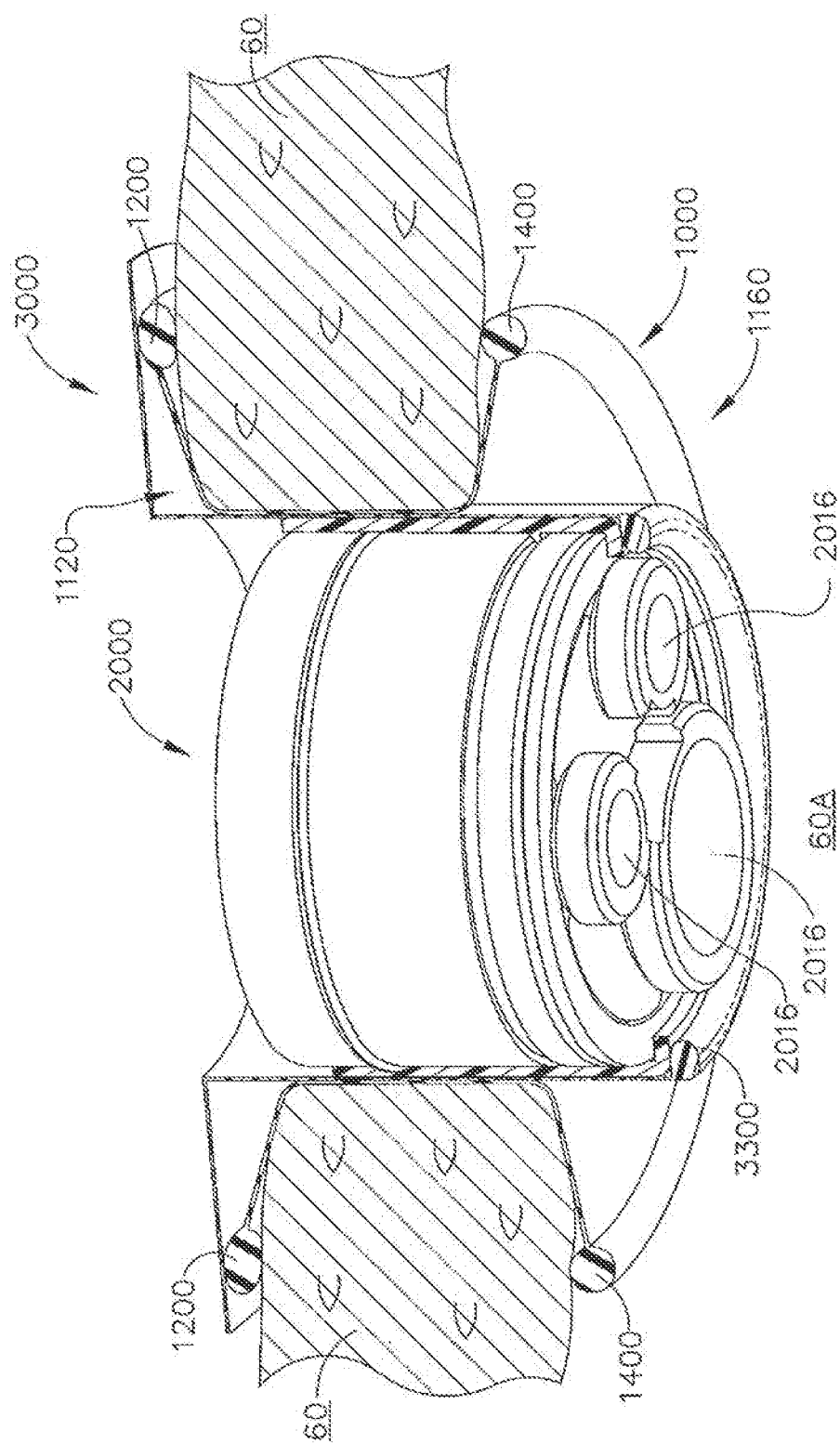
FIG. 9 illustrates the insert, sleeve, and tissue retractor positioned in tissue, with the insert shown inserted into and supported by the sleeve, and the sleeve, in turn, supported in the tissue retractor, with the sleeve and retractor shown in half section, and FIG. 9 illustrating the sleeve having a length longer than the axial length of the retractor, such that the sleeve can be positioned at various depths within the retractor, and such that in FIG. 9 the distal portion of the insert is shown positioned below the abdominal wall, and the distal portion of the insert abutting a retention feature in the form of an internal lip at the distal end of the sleeve, the retention feature preventing the insert from being pushed through the sleeve and into the abdominal cavity, and the lip facilitating removal of the insert with the sleeve when the sleeve is withdrawn from the flexible retractor.
Figure 10:
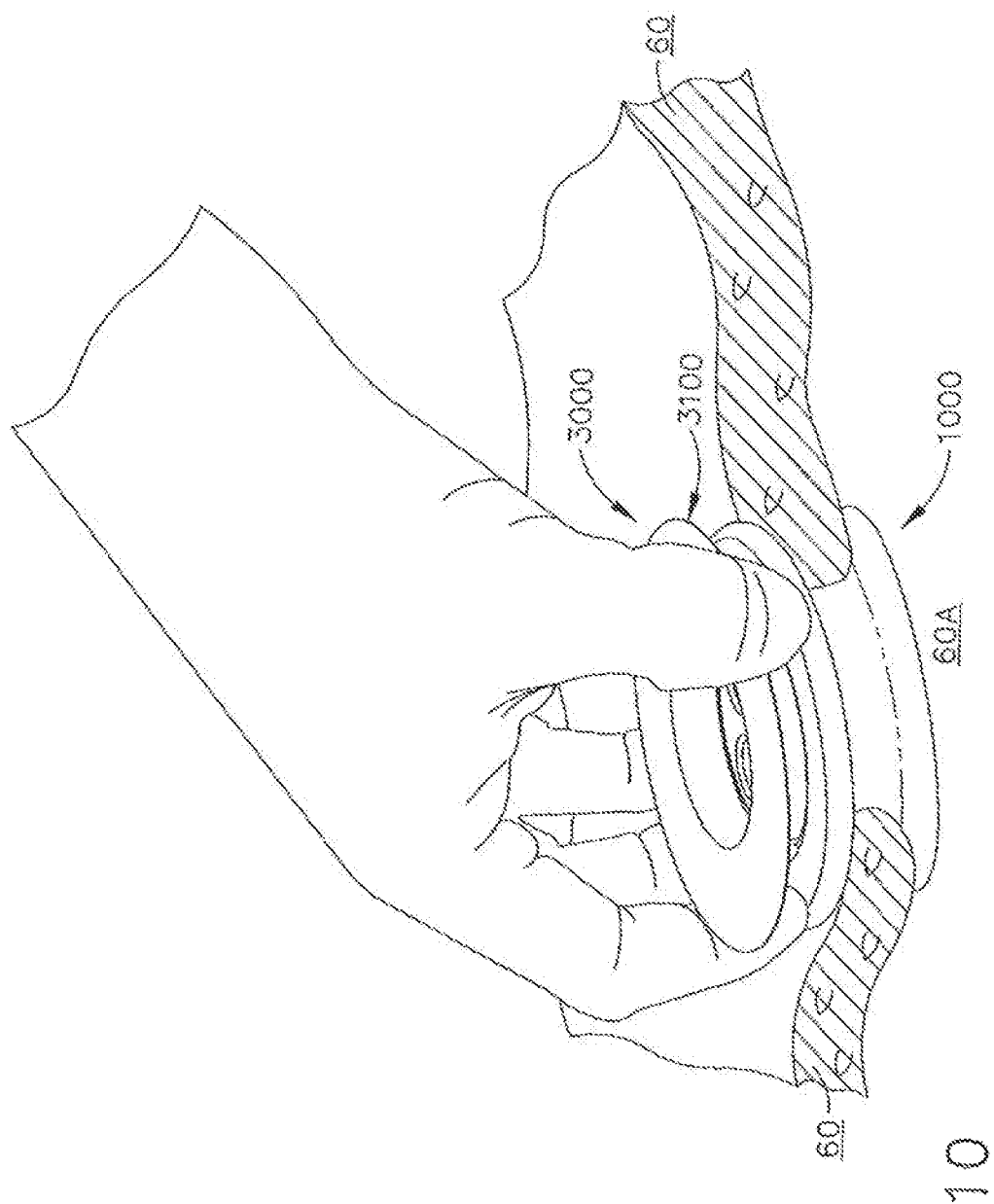
FIG. 10 is a perspective view illustrating how the sleeve and insert can be removed by fingers of a single hand grasping the edges of the sleeve and lifting the sleeve proximally (upward in FIG. 10), with the insert retained by the sleeve and the insert being removed along with the sleeve when the sleeve is withdrawn from the retractor, and with the retractor left in place in the incision.
Figure 11:
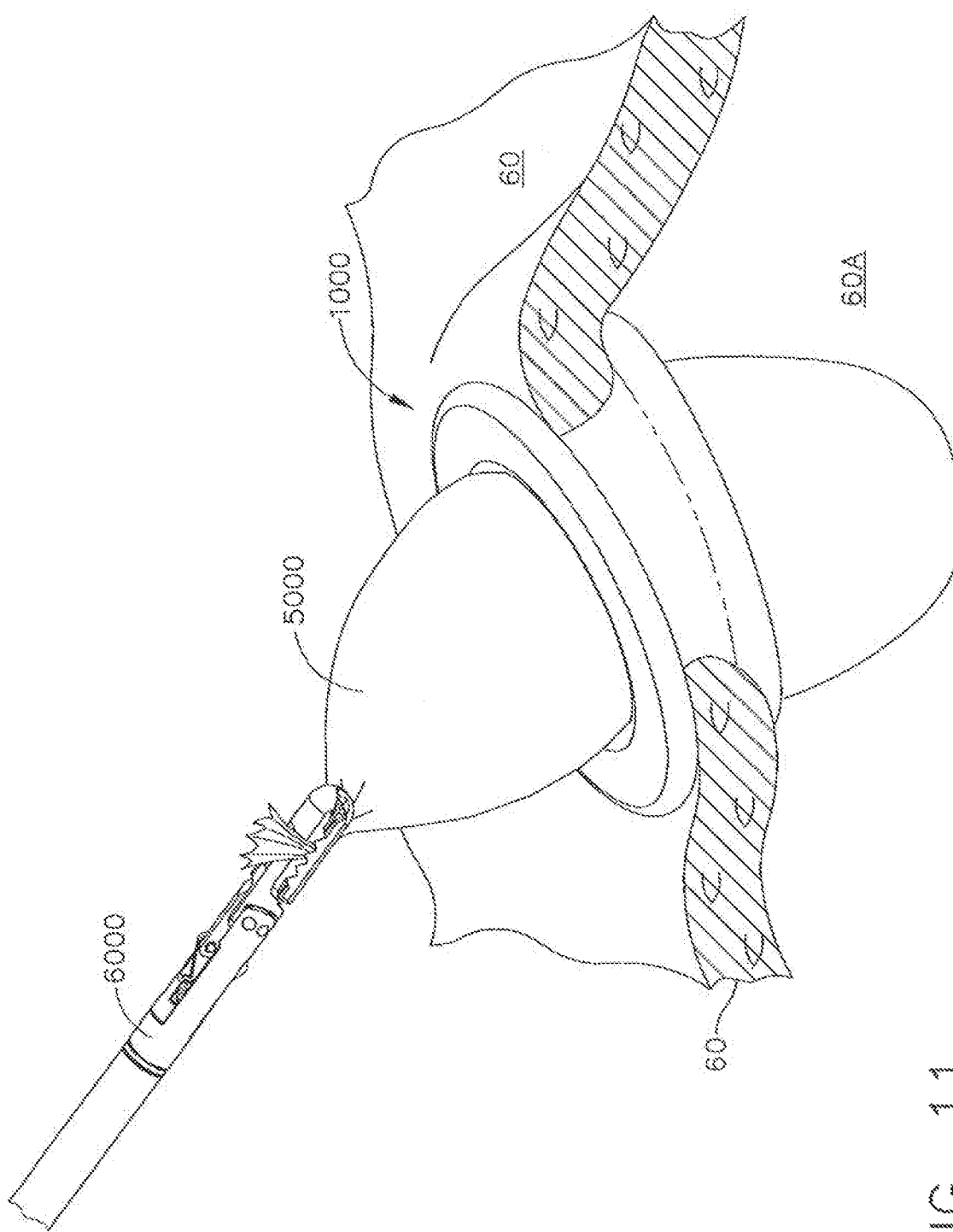
FIG. 11 is a perspective view showing how, once the sleeve and insert have been removed from the flexible retractor, a specimen and/or specimen bag can be removed from the body through the flexible retractor.
Figure 12:
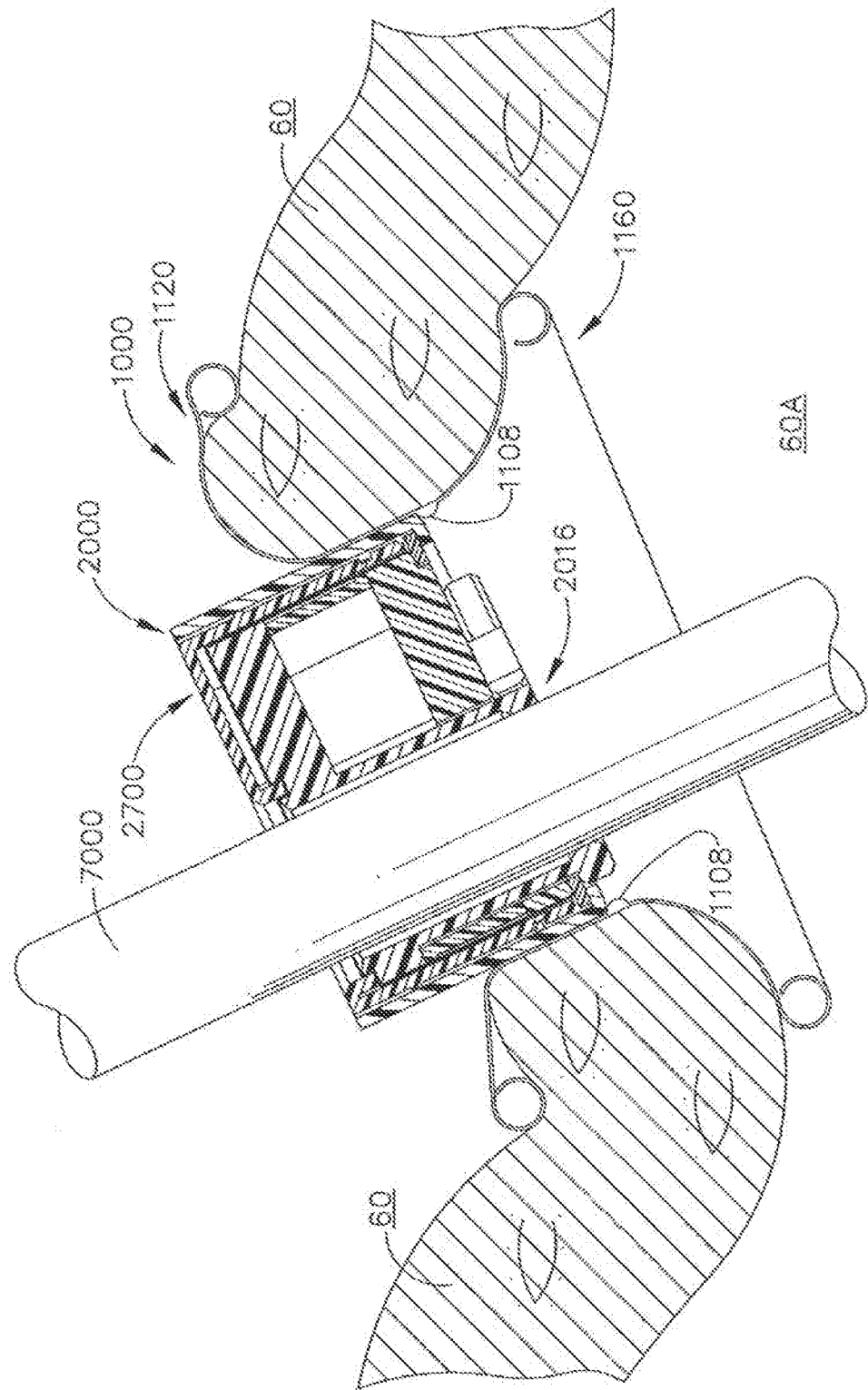
FIG. 12 is a cross-sectional schematic illustration of an embodiment where an insert is disposed within a flexible retractor, where the flexible retractor has an internal retention feature in the form of an internal rib for retaining the insert at a desired depth within the retractor, and FIG. 12 illustrating how the insert's flexible support within the retractor allows an instrument extending through the insert to pivot the insert itself, such as to provide an improved range of motion of the instrument over seals mounted above or below the retractor.
Figure 13:
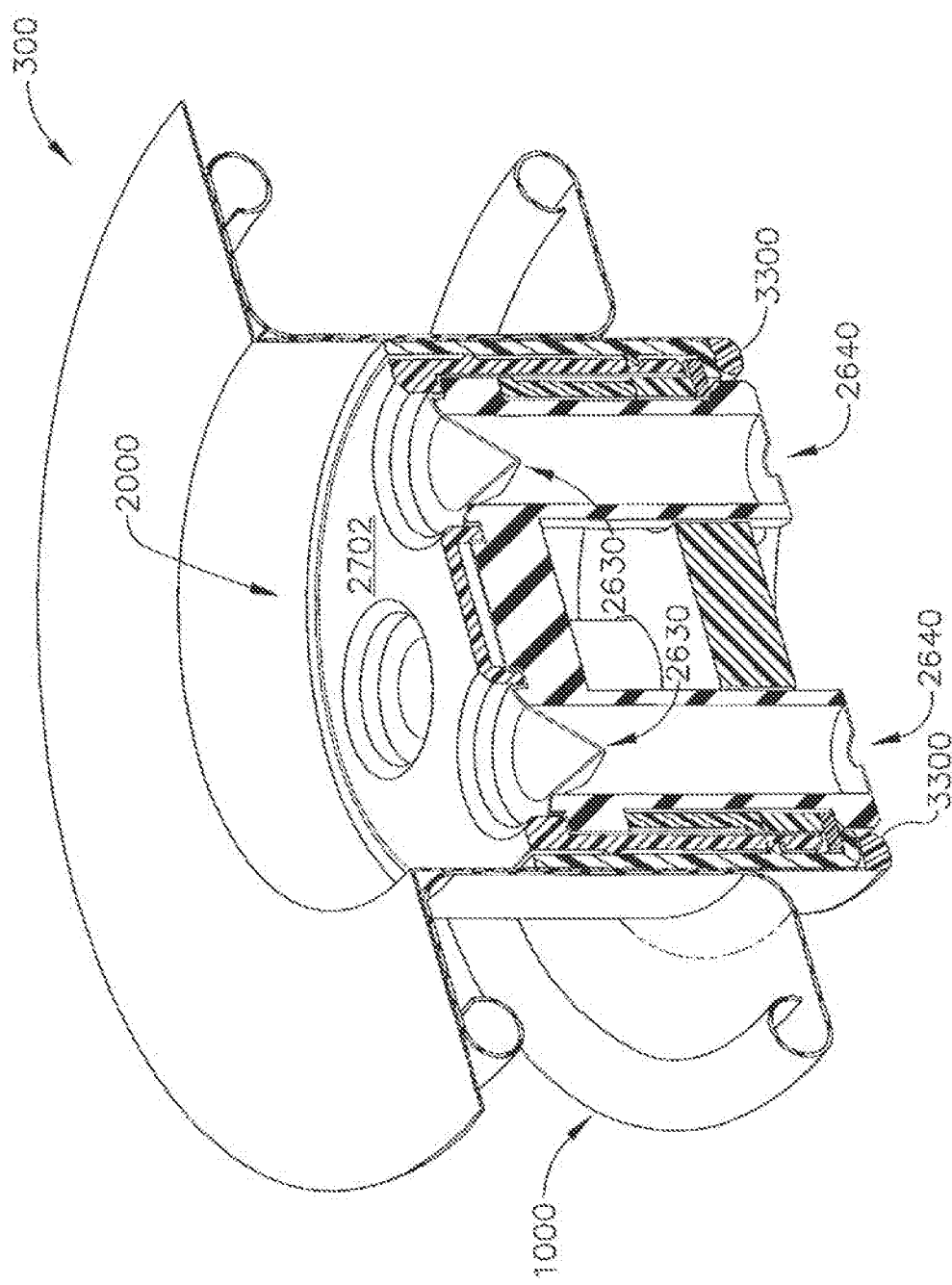
FIG. 13 provides a schematic cross-sectional illustration of an insert, sleeve, and retractor, where the insert includes zero closure seals in the form of duckbill seals at the proximal end of the insert for sealing instrument access channels when no instrument is inserted through the channel, and instrument seals in the form of septum seals for sealing about instruments inserted into the instrument channels.

Referring to FIGS. 3 and 4, the insert 2000 shown comprises an insert assembly. The insert assembly is shown comprising an outer body portion 2100, a bearing member 2200, an inversion constraint member 2300, a spacer 2400, an elastomeric instrument channel member 2500, a membrane seal 2600, and an inner housing 2700, as described mon fully below.

Outer body portion 2100 is shown in the form of a generally cylindrical shell having a generally cylindrical outer surface 2110, an inner surface 2112, a distal ledge 2120 extending radially inwardly from surface 2112, and an internal surface feature, such as a circumferentially extending protrusions 2114.

The outer body portion 2100 may be a generally rigid, hard shell formed of a suitable material, such as polyethylene or other suitable medical grade materials, so that when the insert 2000 is inserted into the flexible retractor 1000, the outer body portion 2100 does not deform to any significant degree, hut instead acts to stretch or otherwise expand the flexible retractor to maintain the passageway 1104 in a desired shape and size, or to provide the passageway with a predetermined size and shape.

The outer body portion 2100 shown may inserted into the retractor to deform the portion of the retractor spaced from and intermediate the rings 1200 and 1400. The outer body portion 2100 can be sized and shaped to pass through one or both rings 1200 and 1400 without deforming the rings. For instance, outer body portion 2100 may have a generally cylindrical outer surface having an outer diameter smaller than the inner diameter of ring 1200, and the outer surface can be sized to radially and circumferentially stretch the portion of the retractor associated with passageway 1104. Accordingly, the insert 2000 may provide the passageway 1104 extending through the incision with a generally circular cross-section of predetermined diameter. The advantages of ease of insertion of a flexible retractor are retained, while preventing the passageway 1104 from being narrowed or constricted by the incision. In addition, an insert having a generally cylindrical configuration provides a generally circular opening through the retractor, with a circle providing the maximum area per unit of perimeter length. A generally circular cross-section of the insert also allows for ease in providing for rotation of a portion of the insert, such as with respect to the outer surface of the insert and/or the retractor.

In one embodiment, the outer diameter of the body portion 2100 may be sized to be slightly larger than the inner diameter of passageway 1104 when retractor is free standing, without the insert 2000 disposed in the passageway 1104. After the retractor 1000 has been inserted into an incision, the insert 2000 may be inserted into retractor 1000. The insert 2000 may be sized to stretch the retractor, to at least slightly enlarge the passageway 1104, and the insert 2000 can frictionally engage the internal surface of passageway 1104. The insert 2000 can act to hold open the passageway 1104 against the compressive forces of the incision acting on the retractor 1000.

What is claimed:

1. A flexible tissue retractor for insertion of laparoscopic instruments, the tissue-retraction device comprising:
   a flexible member comprising a proximal end and a distal end, a first outer exposed portion defining a first plane along a top surface thereof at the proximal end, a first inner exposed portion defining a second plane along a bottom surface thereof at the distal end, and a third portion extending in a distal direction from the first outer exposed portion to the first inner exposed portion such that the third portion interconnects the first outer exposed portion to the first inner exposed portion, the third portion defining a passageway along at least a portion thereof between the first outer exposed portion and the first inner exposed portion; and an insert disposed within the passageway, the insert comprising at least two predefined instrument conduits defined through a top portion of the insert, the conduits extending in the distal direction to corresponding exits defined through a bottom portion of the insert, the insert being wholly within the respective first and second planes defined by the first outer exposed portion and the first inner exposed portion such that the conduits do not extend beyond the first and second planes, the conduits interconnecting the top portion of the insert with a bottom portion of the insert, and the conduits being at least two different sizes.

2. The flexible tissue retractor of claim 1, wherein the flexible member is made of an elastic material.

3. The flexible tissue retractor of claim 2, wherein the flexible member is configured to allow the conduits to be movable to an angle that is not parallel to the first or second plane.

4. The flexible tissue retractor of claim 1, wherein the flexible tissue retractor further comprises a first outer ring that surrounds the first outer portion.

5. The flexible tissue retractor of claim 4, wherein and the second inner portion comprises a second inner ring that surrounds the second inner portion.

6. The flexible tissue retractor of claim 1, wherein the third portion further comprises a first surface and a second surface, the first surface facing radially inwardly and the second surface facing radially outwardly.

7. The flexible tissue retractor of claim 6, wherein the passageway is defined at least in part by a portion of the first surface.

8. A flexible tissue retractor for insertion of laparoscopic instruments, the tissue-retraction device comprising:

a flexible member comprising a proximal end and a distal end, a first outer exposed portion defining a first plane along a top surface thereof at the proximal end, a first outer ring that surrounds the first outer exposed portion, a first inner portion defining a second plane along a bottom surface thereof at the distal end, a second inner ring that surrounds the first inner exposed portion, and a third portion extending in a distal direction from the first outer exposed portion to the first inner exposed portion such that the third portion interconnects the first outer exposed portion to the first inner exposed portion, the third portion defining a passageway along at least a portion thereof between the first outer exposed portion and the first inner exposed portion; and an insert disposed within the passageway, the insert comprising at least two predefined instrument conduits defined through a top portion of the insert, the conduits extending in the distal direction to corresponding exits defined through a bottom portion of the insert, the insert being wholly within the respective first and second planes defined by the first outer exposed portion and the first inner exposed portion such that the conduits do not extend beyond the first and second planes, the conduits interconnecting the top portion of the insert with a bottom portion of the insert, and the conduits being at least two different sizes.

9. The flexible tissue retractor of claim 8, wherein the flexible member is made of an elastic material.

10. The flexible tissue retractor of claim 9, wherein the flexible member is configured to allow the conduits to be movable to an angle that is not parallel to the first or second plane.

11. The flexible tissue retractor of claim 8, wherein the third portion further comprises a first surface and a second surface, the first surface facing radially inwardly and the second surface facing radially outwardly.

12. The flexible tissue retractor of claim 11, wherein the passageway is defined at least in part by a portion of the first surface.

13. A flexible tissue retractor for insertion of laparoscopic instruments, the tissue-retraction device comprising:

a flexible member comprising a proximal end and a distal end, a first outer exposed portion defining a first plane along a top surface thereof at the proximal end, a first outer ring that surrounds the first outer exposed portion, a first inner exposed portion defining a second plane along a bottom surface thereof at the distal end, a second inner ring that surrounds the first inner exposed portion, and a third portion extending in a distal direction from the first outer exposed portion to the first inner exposed portion such that the third portion interconnects the first outer exposed portion to the first inner exposed portion, the third portion comprising a first surface facing radially inwardly and a second surface facing radially outwardly, the first surface defining a passageway along at least a portion thereof between the first outer exposed portion and the first inner exposed portion; and an insert disposed within the passageway, the insert comprising at least two predefined instrument conduits defined through a top portion of the insert, the conduits extending in the distal direction to corresponding exits defined through a bottom portion of the insert, the insert being wholly within the respective first and second planes defined by the first outer exposed portion and the first inner exposed portion such that the conduits do not extend beyond the first and second planes, the conduits interconnecting the top portion of the insert with a bottom portion of the insert, and the conduits being at least two different sizes.

14. The flexible tissue retractor of claim 13, wherein the flexible member is made of an elastic material.

15. The flexible tissue retractor of claim 14, wherein the flexible member is configured to allow the conduits to be movable to an angle that is not parallel to the first or second plane.

* * * * *